United States Patent
Wernevi et al.

(10) Patent No.: US 9,710,761 B2
(45) Date of Patent: Jul. 18, 2017

(54) METHOD AND APPARATUS FOR DETECTION AND PREDICTION OF EVENTS BASED ON CHANGES IN BEHAVIOR

(71) Applicant: Nordic Technology Group Inc., Providence, RI (US)

(72) Inventors: Erik Wernevi, Providence, RI (US); Sheldon Apsell, Newton Centre, MA (US)

(73) Assignee: Nordic Technology Group, Inc., Providence, RI (US)

( * ) Notice: Subject to any disclaimer, the term of this patent is extended or adjusted under 35 U.S.C. 154(b) by 270 days.

(21) Appl. No.: 13/840,155

(22) Filed: Mar. 15, 2013

(65) Prior Publication Data

US 2014/0279740 A1     Sep. 18, 2014

(51) Int. Cl.
  G06F 15/18      (2006.01)
  G06N 99/00      (2010.01)
  G06F 19/00      (2011.01)

(52) U.S. Cl.
  CPC ......... *G06N 99/005* (2013.01); *G06F 19/345* (2013.01)

(58) Field of Classification Search
  None
  See application file for complete search history.

(56) References Cited

U.S. PATENT DOCUMENTS

| | | |
|---|---|---|
| 6,095,985 A | 8/2000 | Raymond |
| 6,108,685 A | 8/2000 | Kutzik |
| 6,201,476 B1 | 3/2001 | Depeursinge |
| 6,524,239 B1 | 2/2003 | Reed |
| 6,611,206 B2 | 8/2003 | Eshelman |
| 6,856,832 B1 | 2/2005 | Matsumura |
| 6,941,239 B2 | 9/2005 | Unuma |
| 7,001,334 B2 | 2/2006 | Reed |
| 7,202,791 B2 | 4/2007 | Trajkovic |
| 7,369,680 B2 | 5/2008 | Trajkovic |
| 7,502,498 B2 | 3/2009 | Wen |
| 7,552,030 B2 | 6/2009 | Guralnik |

(Continued)

OTHER PUBLICATIONS

He et al. "Falling-Incident Detection and Alarm by Smartphone with Multimedia Messaging Service (MMS)", E-Health Telecommunication Systems and Networks, 2012, 1, pp. 1-5.*

(Continued)

*Primary Examiner* — Li-Wu Chang
(74) *Attorney, Agent, or Firm* — Locke Lord LLP (57) ABSTRACT

A computer-implemented process for detecting and predicting events occurring to a person, includes: observing, using a sensor, a reading of a parameter of a body part of the person which is one of: horizontal location, vertical height, orientation, velocity, and time of observation, wherein the reading corresponds to less information than needed to define the person's posture; receiving the reading into a computer memory; determining from the received reading a pattern of behavior; detecting a change in behavior; identifying from the change in behavior a combination of one or more readings corresponding to an abnormal event; and producing an alert signal when the combination of one or more readings corresponding to the abnormal event is identified. The process may be practiced using a computing machine including a computer memory; a sensor; and a computer processor.

24 Claims, 5 Drawing Sheets

(56) References Cited

U.S. PATENT DOCUMENTS

| | | | |
|---|---|---|---|
| 7,586,418 | B2 | 9/2009 | Cuddihy |
| 7,589,637 | B2 | 9/2009 | Bischoff |
| 7,847,682 | B2 | 12/2010 | Jung |
| 7,905,832 | B1 | 3/2011 | Lau |
| 7,937,461 | B2 | 5/2011 | Kutzik |
| 8,120,498 | B2 | 2/2012 | Dishong |
| 8,223,011 | B2 | 7/2012 | Noury |
| 8,237,558 | B2* | 8/2012 | Seyed Momen et al. ............. 340/539.11 |
| 8,321,562 | B2 | 11/2012 | Kutzik |
| 8,890,937 | B2 | 11/2014 | Skubic |
| 2004/0223629 | A1* | 11/2004 | Chang ............. G06K 9/00228 382/118 |
| 2005/0068169 | A1 | 3/2005 | Copley |
| 2006/0281979 | A1 | 12/2006 | Kim |
| 2007/0296571 | A1* | 12/2007 | Kolen ............. A61B 5/0002 340/539.11 |
| 2008/0162088 | A1 | 7/2008 | DeVaul |
| 2008/0266118 | A1 | 10/2008 | Pierson |
| 2010/0302043 | A1 | 12/2010 | Skubic |
| 2011/0118613 | A1 | 5/2011 | Yokoyama |
| 2011/0295080 | A1 | 12/2011 | Chen |
| 2012/0123277 | A1 | 5/2012 | Blaha |
| 2014/0233356 | A1 | 8/2014 | Pattikonda |
| 2014/0235969 | A1* | 8/2014 | Van Der Heide et al. ... 600/301 |
| 2014/0279740 | A1 | 9/2014 | Wernevi |
| 2016/0089047 | A1 | 3/2016 | Jonnada |

OTHER PUBLICATIONS

Yang et al. ("A Review of Accelerometry-Based Wearable Motion Detectors for Physical Activity Monitoring", Sensors 2010, 10, 7772-7788.*

Ahmed et al. "On Use of a Nominal Internal Model to Detect a Loss of Balance in a Maximal Forward Reach", J Neurophysiol, 2007, pp. 2439-2447.*

Kiryati et al. "Real-time Abnormal Motion Detection in Surveillance Video", ICPR 2008, pp. 4.*

Cheng H., Tan, P.-N., Potter, C., and Klooster, S.A., Detection and Characterization of Anomalies in Multivariate Time Series, Proceedings of the 2009 SIAM International Conference on Data Mining, 2009, in SDM, pp. 413-424.

Nixon, M., and Aguado, A., "Feature Extraction & Image Processing for Computer Vision", 3rd edition, Academic Press, 2012, Oxford, UK.

Johnson, R. A., and Wichern, D. W., Applied Multivariate Statistical Analysis, 6th edition, Prentice Hall, 2007.

Cheng et al., Detection and Characterization of Anomalies in Multivariate Time Series, Proceedings of the 2009 SIAM Internaitonal Conference on Data Mining, 2009, in SDM, pp. 413-424.

Nixon et al., "Feature Extraction & Image Processing for Computer Vision," 3rd Edition, Academic Press, 2012, Oxford, UK.

Johnson et al., "Applied Multivariate Statistical Analysis," 6th Ed., Prentice Hall, 2007.

He et al., "Falling-Incident Detection and Alarm by Smartphone with Multimedia Messaging Service (MMS)", E-Health Telecommunication Systems and Networks, 2012, 1, 1-5.

Yang et al., "A Review of Accelerometry-Based Wearable Motion Detectors for Physical Activity Monitoring", Sensors 2010, 10, 7772-7788.

Kiryati et al., "Real-time Abnormal Motion Detection in Surveillance Video", ICPR 2008, pp. 4.

Ahmed et al., "On Use of Nominal Internal Model to Detect a Loss of Balance in a Maximal Forward Reach," J Neurophysiol. 2007, pp. 2439-2447.

Abbatea et al., "A Smartphone-based Fall Detection System," Pervasive and Mobile Computing, 2012 (8), pp. 883-889.

Anania et al., "Development of a Novel Algorithm for Human Fall Detection Using Wearable Sensors," IEEE Sesnors, 2008 Conference (4 pages).

Ning Jia, "Detecting Human Falls with a 3-Axis Digital Accelerometer," Analog Dialogue 43-07, Jul. 2009 (7 pages).

Habib et al., "Smartphone-Based Solutions for Fall Detection and Prevention: Challenges and Open Issues," Sensors 2014, 14, 7181-7208.

Igual et al., "Challenges, issues and trends in fall detection systems," BioMedical Engineering OnLine 2013, 12:66 (24 pages).

Mirelman et al., "Body-Fixed Sensors for Parkinson Disease," JAMA The Journal of the American Medical Association • Sep. 2015 [https://www.researchgate.net/publication/281483338] (3 pages).

Wilson et al., "Recognition and Interpretation of Parametric Gesture," M.I.T. Media Laboratory Perceptual Computing Section Technical Report No. 421 Submitted to: International Conference on Computer Vision, 1998 (8 pages).

Xu et al., "Exploring Techniques for Vision Based Human Activity Recognition: Methods, Systems, and Evaluation," Sensors 2013, 13, 1635-1650.

Pannurat et al., "Automatic Fall Monitoring: A Review," Sensors 2014, 14, 12900-12936.

Wu et al., "A Detection System for Human Abnormal Behavior," Projects No. CUHK 4163/03E.

* cited by examiner

METHOD AND APPARATUS FOR DETECTION AND PREDICTION OF EVENTS BASED ON CHANGES IN BEHAVIOR

BACKGROUND

The present invention relates to behavior modeling and how to detect, or predict, an occurrence of adverse events based on observed changes in a behavior.

Elderly people suffer from a number of age-related health problems. These include, but are not limited to, diminished visual acuity, difficulty with hearing, impairment of tactile senses, short and long term memory loss, lack of stability resulting in frequent falls, other chronic conditions, etc. All of these problems result in serious concerns regarding the safety of elderly people living at home, particularly if they are living alone. Many studies have shown the benefits of getting help quickly after certain types of adverse events. For example, in the case of falls, getting help within one hour is widely believed to substantially reduce risk of both hospitalization and death.

Over a long period of time, there have been numerous attempts in the arts to address this long-standing problem related to elder care by technological means. Early monitoring systems employed a pendent or wristband worn by the person being monitored that contained a medical alarm button. When the wearer pressed the button on the pendent, it sent a signal to a base station connected to a call center by means of the public telephone network.

Devices to detect unusual behaviors, including behaviors that may be hazardous or indicate a bad outcome of some condition, continued to evolve. Wearable sensors were added to detect falling events, for example. Some systems include sensors to detect vital signs such as pulse, heartbeat, and temperature.

Another approach is using passive sensors in the home to detect critical events. Using this approach does not require active participation by the user; the person monitored is simply free to go about their daily activities without having to change their routines.

Other approaches detect isolated acts or behavior patterns through the use of motion sensors and/or sensors linked to different articles in the household such as light switches, door locks, toilets etc.

Another technique for passive sensing is to use cameras and different methods for recognizing patterns of behavior.

U.S. Pat. No. 6,095,985 describes a known system that directly monitors the health of a patient as opposed to indirectly, or behaviorally, detecting a medical problem. Rather, it does so by employing a set of physiological sensors placed on the patient's body.

A number of patents, such as U.S. Pat. Nos. 7,586,418, 7,589,637, and 7,905,832 merely monitor activity, as an attribute having a binary value, during various times of day. The assumption is that if the patient is in motion during appropriate times of the day and not in motion during the night, then no medical problem exists. In such systems, if the patient takes a nap during the day or gets up to go to the bathroom at night, a false alarm will be generated. Another patent, U.S. Pat. No. 8,223,011 describes a system wherein for each patient predetermined rules are established for each daily block of time and place within the residence. All of the patents referred to above require some a priori knowledge of the patient, the patient's habits, and/or the patient's environment, either for determining individual habits or for setting detection and/or significance thresholds for sensors or processed sensor outputs.

A number of other systems described in U.S. patents add some degree of adaptive learning to help construct a behavior profile. For example, U.S. Pat. No. 7,552,030 describes an adaptive learning method to generate a behavior model. The method is shown to generate specific individual behavior models for specific predetermined actions such as opening a refrigerator door. Another patent, U.S. Pat. No. 7,847,682 describes a system that senses abnormal signs from a daily activity sequence by using a preset sequence alignment algorithm and comparing a sequence alignment value obtained by the system with a threshold value. Other systems described in U.S. patents, such as those described in U.S. Pat. Nos. 7,202,791 and 7,369,680, employ video cameras to generate a graphic image from which feature extraction algorithms are employed to use as a basis for building up a behavior profile. The systems and methods described define vertical distance, horizontal distance, time, body posture and magnitude of body motion as the features to be extracted from the video image.

SUMMARY

Aspects of embodiments of the invention include an entirely new approach to monitoring safety of the elderly. Aspects of embodiments of the invention can detect a broad range of current health problems or potential future health problems. An exemplary embodiment of the invention includes aspects that detect unusual behaviors that are indicators of underlying health problems. These indicators can be detected by remote observation of elements of a person's behavior.

Another exemplary embodiment of the invention includes aspects to determine a pattern, or absence of pattern, of behavior, in how an activity is performed by a person. Changes to the pattern, or variations to some small detail in the pattern that may indicate the occurrence of, or imminent occurrence of, an event can be detected. According to one aspect of an embodiment of the invention, a sequence of deviations in how an activity, or activities, are performed by a person are assessed based on observed movements of one or more body parts and a determination is made, based upon detection of a deviation from the normal pattern, that an adverse event has occurred, or is likely to occur, and an appropriate response for assistance or further investigation is triggered.

In accordance with some aspects of embodiments of the invention, the behavior of the user is captured through sequential observation of one or more body parts of the user based on some combination of horizontal location, vertical height, orientation, velocity, and time of observation of the one or more body parts. The observed data is used to continuously create and update a behavior profile against which future observations are compared. Correlation is used to determine a pattern of behavior for the one or more body parts. Events are detected, or possible future events predicted, by detecting changes in the observed pattern. Significant changes in behavior are indicated through lack of correlation, either in the overall behavior pattern, or in some detail of the behavior pattern. For example, the pattern may be formed from the observations of a daily walk from the bedroom to the kitchen. A deviation may be indicated by observations resulting from the omission of the walk, or a deviation may be indicated by observations resulting from a limp detected in one leg. At any time, if a minimum set of data is determined to deviate, in a pattern that is inconsistent with past observed data and, or, recorded past behavior profile, further data is collected to determine if the condition signifies an abnormal event that requires that an alert be issued.

The observed deviation from normal behavior may not correlate to a health condition with readily observable symptoms. But it may, in fact, correlate to the initial stages of a health problem that in the future will show readily detectable symptoms. Medical personnel should therefore further investigate deviations from normal behavior.

An exemplary embodiment of the invention uses no a priori information about the user and can with a sufficient number of past observations determine if an adverse event has occurred or if it is likely to occur in the future, and issue an appropriate response for assistance or further investigation.

While there are numerous advantages to various aspects of embodiments of the invention, four advantages include:
1. This method does not require any active participation by the person being monitored;
2. This method does not require any a priori knowledge of the person or the person's environment;
3. This method does not require knowledge of the cause of the problem; and
4. This method is effective over a broad range of medical or health initiated problems.

The present inventors have observed a number of limitations associated with conventional systems and methods, overcome by the foregoing and other advantages of aspects of embodiments of the invention. Some such limitations are noted here.

Medical alarm button systems depend upon the active participation of the wearer. If the wearer does not recognize that assistance was required or if the wearer is not conscious, no help will be summoned. Other, similar systems exhibit the same limitation.

Wearable sensors suffer from limitations arising from failures of patient compliance; to be effective in providing continuous safety monitoring, they must be worn continuously. With wearable sensors there is also in general a trade-off between ease of wearing and accuracy. For example, a movement sensor worn around the torso often has a higher specificity and sensitivity than a sensor worn around the wrist or the neck; however, this is at the expense of wearability. In practice, wearable sensors have proven to be very unreliable and as a result these alarms are often ignored.

Vital sign sensors frequently suffer from the same limitation as other wearable sensors of lack of patient compliance and, moreover, vital sign sensors are typically best suited to address specific conditions.

Known passive sensor systems deployed in homes are designed to detect specific events and consequently can address only a small segment of the health problems that affect the elderly population.

Passive environmental sensors, including motion sensors and sensors detecting the use or movement of common household articles, share the drawback that the data generated is often coarse. As a result, it is difficult, if not impossible, to draw conclusions with a high degree of confidence about changes in behavior that may indicate critical events without having to outfit the living environment with such a great number of sensors that real world installations outside of a laboratory environment often become impractical.

Other systems that study behavior patterns at an aggregate level, such as a daily activity sequence, suffer from issues where abnormal patterns of behavior are manifested in how an activity is performed, rather than when, or if, the activity is performed, as aggregate data about the behavior of the person, including, but not limited to, the time-window an activity is done, a sequence of activities etc., may not change, even though an individual may already be exhibiting abnormal behavior that can be detected in more subtle activity and body part movement patterns.

In the case of systems which perform body posture analysis, body posture analysis may detect some falls, but it does not address well situations where very different behaviors are performed with similar body posture and it is much too coarse to detect more subtle changes in behavior that may precede an adverse event. For example someone who feels unwell and lies down on a sofa could easily be confused for someone who is reading on a sofa, as a result not necessarily triggering an alarm until much later when an abnormally long time has passed. Moreover, obtaining sufficient data from practical sensor placements to continuously monitor body posture is difficult, resulting in locations and postures where no data is received and events cannot be detected.

There are many instances where information about body posture may not be available, for example if a person is partly obscured, hence a method that does not require information about the body posture is needed. Also, in some instances it is undesirable that an image is studied, for example if the object and situation studied is a person in a private setting, and it is preferable to be able to extract behavioral information without the need to capture and then interpret an image.

Aspects of embodiments of the invention can employ a method which is versatile enough that it can detect adverse events in different circumstances where only partial information about the body is available, and that the partial information is for different parts of the body in the different circumstances, and that said detection is done in a timely manner. Further, aspects of embodiments of the invention can employ a method to predict possible future adverse events through the study of subtle changes in movements of body parts. Small changes in how activities are performed, that may not be readily apparent to the naked eye, because they may appear slowly over time and therefore may not manifest as large deviations from one day to the next, can hold clues to the health of the user. Such small changes may precede the occurrence of larger adverse events, such as a stroke or a fall, and may warrant a health check-up by an appropriate caregiver or immediate assistance for the user.

A need therefore exists for a system that can give early warning about changes in health to avoid potential future events and can quickly detect the occurrence of an adverse event by detecting subtle changes in behavior. For example, aspects of embodiments of the invention are the first known that integrate plural sensing and/or analyzing elements into a single system capable of automatically creating a sufficient detailed behavior profile to give early warning about potentially adverse changes in health without specific a priori information regarding the person's daily habits or environment.

Aspects of embodiments of the invention detect behaviors by monitoring individual limbs or other body parts, or combinations not otherwise sufficient to determine posture, for activity patterns indicative of behavior patterns. While it may be possible in some instances to determine body posture from aggregated information, aspects of embodiments of the invention can employ aggregated information that is insufficient to identify posture to detect normal and abnormal behavior patterns.

A computer-implemented process for detecting and predicting events occurring to a person, includes: observing, using a sensor, a reading of a parameter of a body part of the person which is one of: horizontal location, vertical height, orientation, velocity, and time of observation, wherein the reading corresponds to less information than needed to define the person's posture; receiving the reading into a computer memory; determining from the received reading a pattern of behavior; detecting a change in behavior; identifying from the change in behavior a combination of one or more readings corresponding to an abnormal event; and producing an alert signal when the combination of one or more readings corresponding to the abnormal event is identified. Numerous variations are possible, as now exemplified.

The computer-implemented process may identify that a future abnormal event is likely to occur. Observing the reading of the parameter of the body part may further comprise sensing the parameter with respect to the person's head. Observing the reading of the parameter of the body part may further comprise sensing the parameter with respect to the person's torso. Observing the reading of the parameter of the body part may further comprise sensing the parameter with respect to one of the person's limbs. Observing the reading of the parameter of the body part may further comprise sensing the parameter with respect to a combination of two or more of the person's head, the person's torso, and one of the person's limbs, wherein the combination is less than needed to define the person's posture. In connection with any of the variations on observing, above, identifying may further comprise identifying the combination of one or more readings corresponding to the abnormal event when at least one other body part is obscured from the sensor. The computer-implemented process may further comprise computing velocity from a sequence of the readings. The computer-implemented process may further comprise identifying a combination of readings corresponding to a normal event. The computer-implemented process including identifying a combination of readings corresponding to a normal event may further comprise identifying a combination of readings representing an activity of daily living. The computer-implemented process including identifying a combination of readings corresponding to a normal event may further comprise learning to differentiate between the normal event and the abnormal event by applying a statistical test to the sequence of readings. The statistical test may be correlation. Observation may further comprise sensing an output of a wearable sensor; sensing an output of one of: a visual camera, infrared camera, and acoustical detector; sensing an output of a radio-wave measuring device; and sensing an output of a light-wave measuring device. Aspects of embodiments of the invention can also include combinations and sub-combinations of the various aspects of embodiments enumerated above, for example using a particular sensor in connection with any of the other combinations.

The process may be practiced using a computing machine including a computer memory; a sensor; and a computer processor. All of the foregoing variations may be practiced on such a computing machine. Moreover, the sensor may be any one or combination of a wearable sensor; a visual camera, infrared camera, and acoustical detector; a radio-wave measuring device; and a light-wave measuring device.

In the following description, reference is made to the accompanying drawings, which form a part hereof, and in which are shown example implementations. It should be understood that other implementations are possible, and that these example implementations are intended to be merely illustrative.

DESCRIPTION OF THE DRAWING

In the Drawing, in which like reference designations indicate like elements.

DETAILED DESCRIPTION

Exemplary embodiments of the present invention will now be described in detail with reference to the accompanying figures. The following section provides general and specific examples of aspects of embodiments of the invention.

Figure 1:
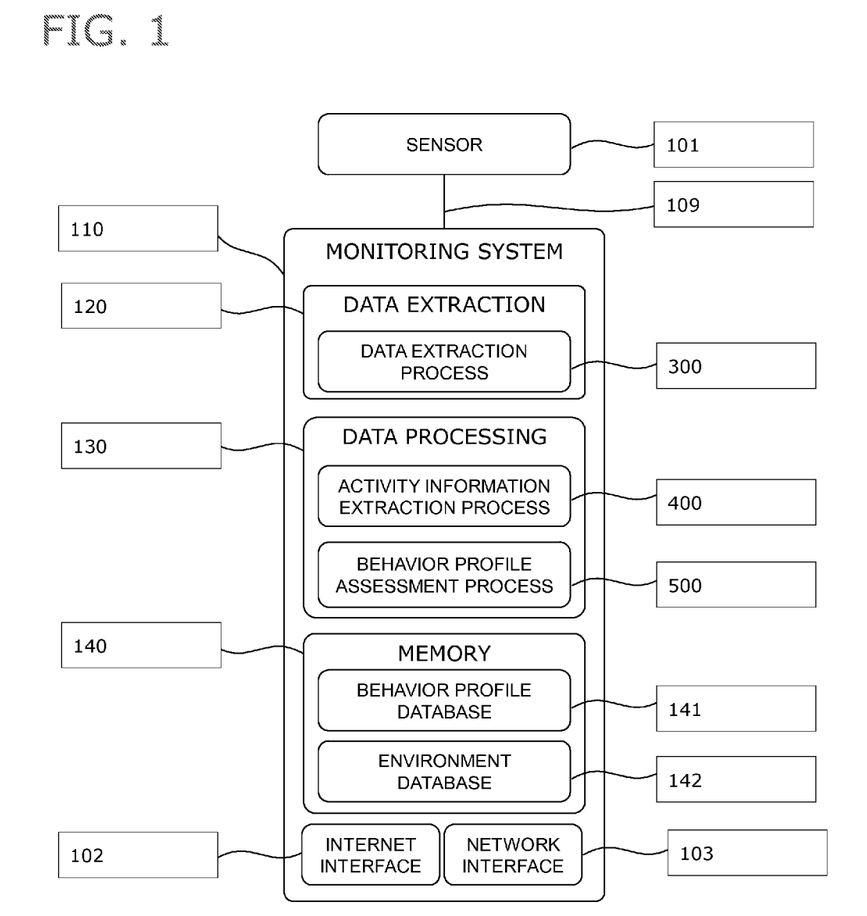
FIG. 1 illustrates a monitoring system according to an exemplary embodiment of the present invention.

FIG. 1 illustrates a monitoring system according to an exemplary embodiment of the present invention. Without losing the essence of the invention, for sake of brevity, the person studied, will henceforth be referred to as "user". The behavior of the user is captured through sequential observation of a, body part, or parts, of the user based on some combination of horizontal location, vertical height, orientation, velocity (velocity being the vector whose values represent speed and direction), and time of observation of said body part, or parts.

The observed data is used to continuously create and update a behavior profile against which future observations are compared. Correlation is used to determine a pattern of behavior for said body part, or parts.

Adverse events are detected, or possible future adverse events predicted, by detecting changes in pattern in the above-observed dimensions for a body part, or parts, that through correlation are determined to indicate significant changes in behavior. At any time, a minimum set of data is determined to deviate when an observed pattern is inconsistent with past observed data, or in a way that cannot reasonably be inferred from past data corresponding to normal behavior.

In FIG. 1, described first, the blocks may be one or more of, or a combination of, software modules; hardware modules; software executing on a general purpose computer including sensors, memory, a processor, and other input and output devices; and, special purpose hardware including sensors, memory, a processor, and other input and output devices. Sensors used can include cameras, and other sensors described in detail in conjunction with FIG. 3, from the outputs of which the measurements of body part parameters can be extracted, as described below.

Referring to FIG. 1, an exemplary monitoring system is shown that includes an event detection system 110, connected to one or more sensors 101, the internet, or phone network, through interface 102, and a local network 103. Sensors 101 record multi-dimensional data of horizontal location, vertical height, orientation, velocity, and time of observation. The data captured is relayed as a continuous data feed 109 to the monitoring system 110. At any given time, from the data feed 109, said multi-dimensional data is extracted by the data extraction process 120, where possible, for the body parts of the observed user. The data extracted by the data extraction process 120 is subsequently processed by data processing 130 for evaluation and to build a behavior profile. A log of events and other data, about the user and the environment the user is in that is determined relevant for event detection and the behavior profile, are stored in memory 140.

Figure 2:
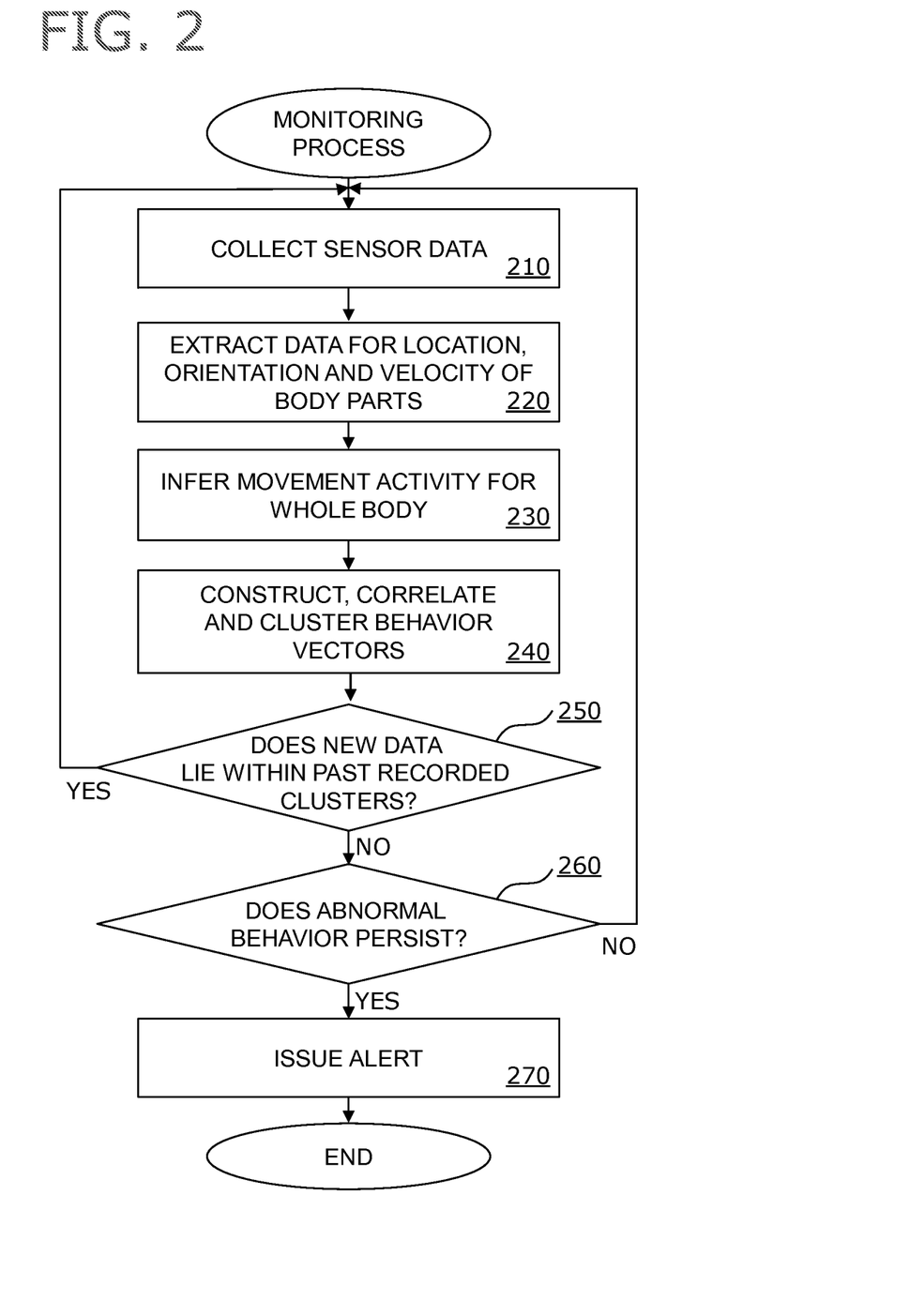
FIG. 2 illustrates a flow chart for an exemplary implementation of the monitoring process of FIG. 1.

FIG. 2 illustrates a flowchart for an exemplary implementation of a method that can be practiced using the system of FIG. 1. In step 210, data is collected, at any given time, about the user's body parts by one or more sensors 101 for horizontal location, vertical height, orientation, velocity, and time of observation. In step 220, available data for different body parts is extracted. The data is associated with different body parts through data collection and, or, historical information on movements. This process is further discussed in conjunction with FIG. 3. In step 230, the activity of the whole body is inferred from observed, and inferred, body part movements. This process is further discussed in conjunction with FIG. 4. In step 240, the activity information data from step 230 is used to construct n-dimensional behavior vectors that are stored in behavior profile database 141. These n-dimensional behavior vectors are evaluated for correlations and clusters that may indicate behavior patterns. This process is further discussed in conjunction with FIG. 5. In step 250, the new n-dimensional behavior vectors from step 240 are compared with a behavior profile constructed with past recorded data, stored in behavior profile database 141, and determining whether or not this new measurement lies within any of the clusters described above. If the new data does lie within any of the clusters described above, then this represents normal behavior and the process starts again at step 210. Further, the above recorded new data is added to the moving averages using an appropriate moving average technique e.g. simple, weighted, or exponential moving average etc., to further refine the normal behavior profile stored in the behavior profile database 141. If the data does not lie within any of the clusters described above, then in step 260, this new measurement is flagged as abnormal and additional data is accumulated. If the additional data collected lies within previously recorded clusters, described above, the process starts again at step 210. In step 270, if the abnormal behavior persists, a warning message is sent to appropriate responders.

Figure 3:
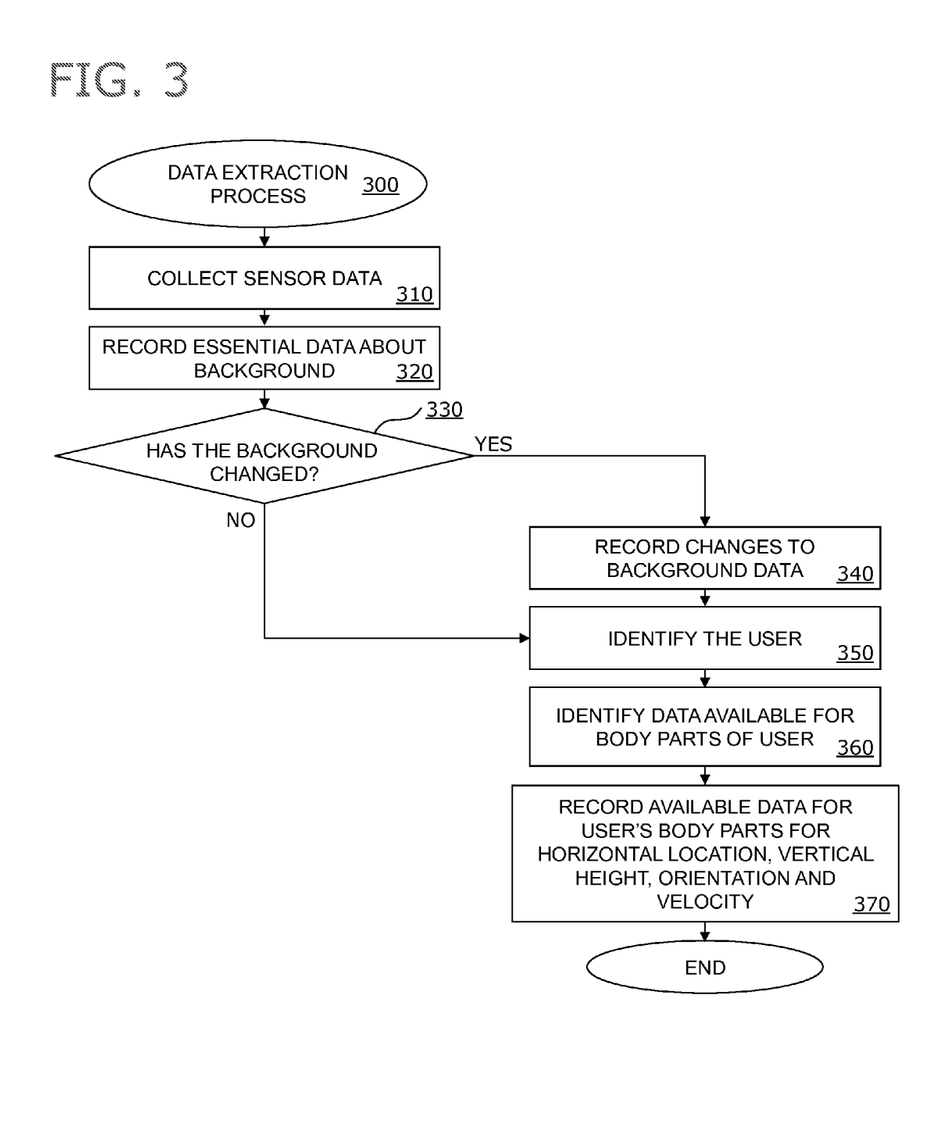
FIG. 3 illustrates a flow chart for an exemplary implementation of the data extraction process of FIG. 1.

FIG. 3 illustrates an exemplary data extraction process 300. In step 310 the sensor data feed 109 is collected from one or more sensors 101. In step 320, a learning process is initialized by recording essential data by the sensor, or sensors, about the environment the user is in. For the purposes of the illustration of this exemplary invention, all objects that are not directly associated with the movement activity of the user are considered background and the terminology background and environment are used interchangeably. This essential data is recorded and stored in the environment database 142 in memory 140. Essential data include, but is not limited to, spatial data, and non-spatial data, e.g. colors, texture, etc., about floors, ceilings, walls, large and small stationary, and non-stationary, objects, as well as sensory data, e.g. light, temperature, barometric pressure, etc. In step 330, new background data is compared to previous background data to determine significant changes to the environment, examples include, but are not limited to, movement of stationary and non-stationary objects, changes in light conditions, and changes in temperature. In step 340, if the background has changed, the type of change is recorded, time stamped and stored in the background environment database 142. In step 350, the sensor data is further processed and data describing the user is identified through a process of a combination of one, or more, of identification of moving objects, suppression of background recorded in step 320, utilization of information about changes recorded to the background in step 340, or by using known methods for feature extraction and identification of the user including, but not limited to, those described in the book *Feature Extraction & Image Processing for Computer Vision,* $3^{rd}$ edition, Nixon, M., and Aguado, A., Academic Press, 2012, incorporated herein by reference. In step 360, observable body parts of the user are identified using data extracted about the user from step 350 and a combination of one or more methods for feature extraction, exemplary methods include, but are not limited to, principal component analysis, thresholding, template matching, etc. In step 370, available data for each body part for horizontal location, vertical height, orientation and velocity, is recorded.

Variations of exemplary embodiments utilize different types of sensor, 101, for data extraction about user and background. Depending on the types of sensor utilized, the exact data captured about a user's body parts may be more or less accurate for observing information on horizontal location, vertical height, orientation, velocity, and time of observation for the respective body parts. The essential data that can be recorded about the environment, i.e. background, will also differ in terms of spatial, and non-spatial, data and sensory data that can be recorded and what environmental information and constraints can be extracted. Notwithstanding these differences in the data extracted, processes for activity information extraction and behavior profile assessment are agnostic as to how the data on body parts and environment have been extracted. Immediately following are exemplary embodiment variations for the data extraction process when using the following different types of sensor categories: wearable sensors, cameras e.g. visual, infrared etc., acoustical detectors, radio-wave measuring devices, or light-wave measuring devices.

In an exemplary implementation variation of sensors 101, using wearable sensors, sensors could be affixed to multiple tracked body parts, each sensor observing data on, one or more of, multi-dimensional data on horizontal location, vertical height, orientation, velocity, and time of observation for the body part the sensor is affixed to. The information may be captured by the sensor through multiple sensor subunits. Sensor subunits may include, but are not limited to, movement, position, vital sign, and environment measurement subunits. Sensors and environment measurement subunits and other subunits may further include, but are not limited to, accelerometers, gyroscopes, barometers, magnetometer, GPS, indoor GPS, vital sign measurement sensors, etc. Alternatively the sensors may capture a subset of said multi-dimensional data about a body part, such as vertical height, orientation, velocity and time of observation, and the remaining multi-dimensional data, an example being the horizontal location, where horizontal location is calculated based on the absolute, or relative, horizontal location of the wearable sensor vis-à-vis the global coordinate system, monitoring system, no, or other relative point of measurement, using a positioning method, e.g. dead-reckoning, received signal strength identification methods, triangulation, directional Bluetooth, Wi-Fi, etc. Although the wearable sensors may not capture all the multi-dimensional data they may be effectively complemented by a non-wearable sensor, as illustrated by the above exemplary implementation, that captures additional complementary multi-dimensional data. Similarly, as described by the above illustrative example, other data that may be captured by a non-wearable sensor could include the vertical height, orientation, or velocity of the wearable sensor may be determined using absolute, or relative, vertical height, orientation, or velocity of the wearable sensor vis-à-vis the global coordinate system, monitoring system, 110, or other relative point of measurement. The wearable sensors may in addition capture information about the environment, e.g. temperature, light conditions, etc. and generate data that can be of assistance in inferring information about the environment e.g. spatial constraints etc. The sensor data feed, 109, may be transmitted to the monitoring device 110 through methods such as radio waves, e.g. CDMA, GSM, Wi-Fi, Near Field Communication, ZigBee, BTLE etc., or light waves, e.g. lasers etc.

In an exemplary implementation variation of sensors 101, using camera sensors, sensors could capture images of the user's body parts and surrounding environment. Exemplary camera sensors may capture different types of images, including, but not limited to visual-, depth-, infrared-, acoustic-images, etc., that enable observation of, one or more of, said multi-dimensional data on horizontal location, vertical height, orientation, velocity, and time of observation for a body part.

In an exemplary implementation variation of sensors 101, using acoustical detectors, sensors could capture and/or generate sounds, audible or ultrasonic, that help in the determination of, one or more of, the multi-dimensional data on, horizontal location, vertical height, orientation, velocity, and time of observation for the body part. Such sounds may include, but are not limited to, body part observation, e.g. locating a voice, identifying walking sounds, detecting an impact noise, or observing the environment, e.g. through detection of environmental changes, presence of other people, breaking sounds, etc.

In an exemplary implementation variation of sensors, 101, using radio-wave measuring sensors, sensors could capture and/or generate radio-waves to identify the user's body parts and surrounding environment. Exemplary radio-wave sensors may generate and/or capture different types of radio-waves using methods, including, but not limited to, radar etc., that enable observation of, one or more of, said multi-dimensional data on horizontal location, vertical height, orientation, velocity, and time of observation for a body part.

In an exemplary implementation variation of sensors 101, using light-wave measuring sensors, sensors could capture and/or generate light-waves to identify the user's body parts and surrounding environment. Exemplary light-wave sensors may generate and/or capture different types of light using methods, including, but not limited to, laser imaging detection and ranging, photo sensors, structured light, etc., that enable observation of, one or more of, said multi-dimensional data on horizontal location, vertical height, orientation, velocity, and time of observation for a body part.

Figure 4:
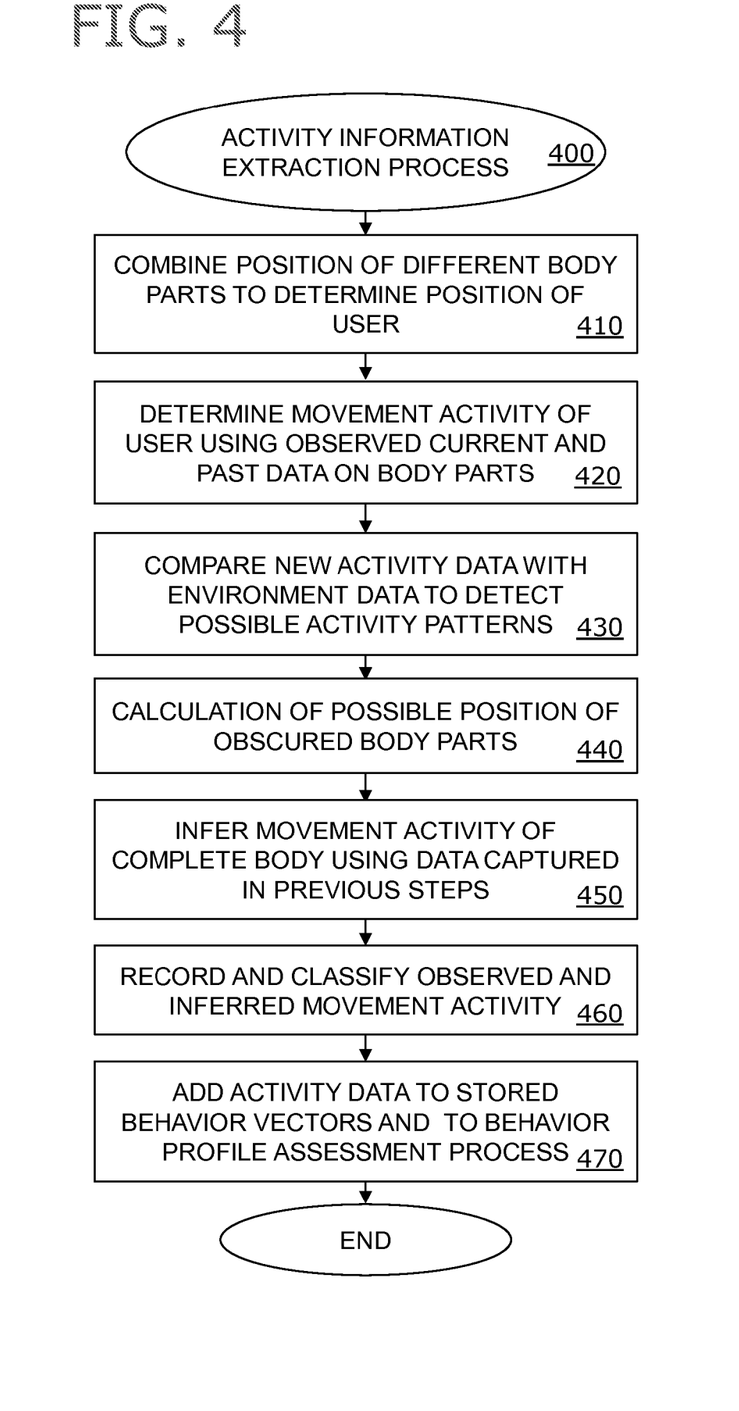
FIG. 4 illustrates a flow chart for an exemplary implementation of the activity information extraction process of FIG. 1.

FIG. 4 illustrates an exemplary activity information extraction process 400. In step 410 data captured in an n-dimensional vector for the user at corresponding time period, for illustration purposes the time period denoted to, for different body parts are combined to determine the position of the user at to. The process has been completed for the preceding time periods t-1, t-2 . . . , etc., and is repeated for the following time periods t1, t2 . . . , etc. In step 420 the sequence of n-dimensional vectors are studied to determine the likely movement activity of the user using observed information on, horizontal location, vertical height, orientation, velocity, and time of observation for the respective body parts. In step 430, observed movement activity is further compared with recent changes in data in environment database 142 to detect possible activity patterns. In step 440, body parts that are fully, or partly, obscured are identified and their possible current positions are calculated using, past recorded positions of body parts and current positions of other identifiable body parts, and, if applicable, any section of the body part that can be observed, as well as, available data on recent changes in background environment, past observed relative body part positions and movement patterns in relation to other body parts, and environmental constraints stored in environment database 142. A likelihood function, with environmental constraints, is used to determine their most probable position. In step 450, the movement activity of the complete body is inferred from the data captured in step 410, 420, 430 and 440. In step 460, the observed, and for unobserved body parts, inferred, movement activity of different body parts, are recorded and, if relevant, classified and labeled. In step 470, all the activity data recorded in step 460 is added to the n-dimensional behavior vectors and stored in memory 140 and used in behavior profile assessment process 500.

Figure 5:
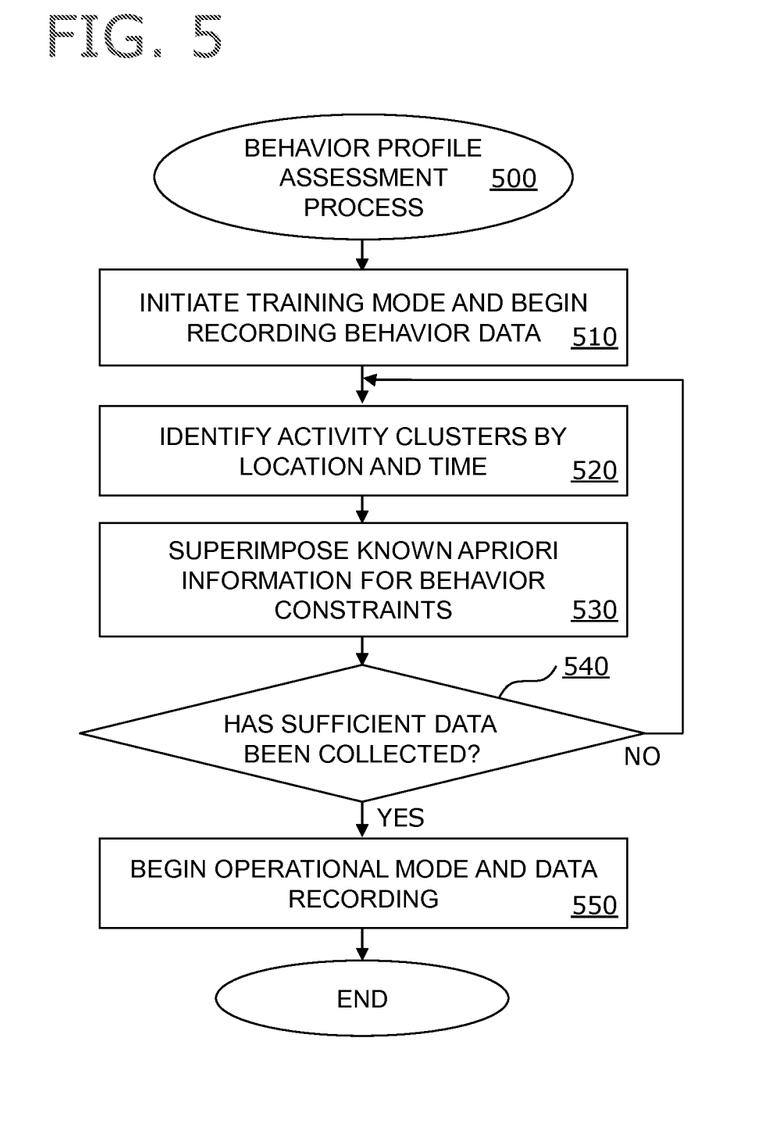
FIG. 5 illustrates a flow chart for an exemplary implementation of the behavior profile assessment process of FIG. 1.

FIG. 5 illustrates an exemplary behavior profile assessment process 500. In step 510, the system is in training mode whereby a habit profile is begun by recording the movement activity recorded by activity information extraction process 400 and generated in step 470 for observed and inferred data for all body parts for horizontal location, vertical height, orientation, velocity, and time of observation. This data is used to form an n-dimensional behavior vector for each time period. In step 520, the system, still in training mode, identifies clusters of the n-dimensional behavior vectors; these clusters are then used to define normal behavior. In step 530, if any a priori knowledge of the subject's behavioral habits is known, they can be superimposed upon the sample vectors to produce a highly constrained dimension in the n-dimensional behavior vector space. The resulting n-dimensional vectors are stored in the behavior profile database 141. In step 540, the training mode is terminated, in an exemplary implementation, this may be done automatically, by employing a standard internal evaluation techniques such as the Davies-Bouldin index, etc., or, alternatively, the training mode may be terminated by imposing some external criteria, e.g. a statistical parameter, arbitrarily imposed period of time, etc. In step 550, the operational mode is begun where new data is recorded periodically during the day, constructing new n-dimensional behavior vectors as described in conjunction with FIG. 2 where the details of the operational mode of the monitoring process are described.

Exemplary statistical techniques that may be employed to correlate body part movements and to construct behavior profiles by means of constructing n-dimensional behavior vectors include, but are not limited to, standard multivariate analysis (see, *Applied Multivariate Statistical Analysis*, 6th edition, Johnson, R. A., and Wichern, D. W., Prentice Hall, 2007, incorporated herein by reference). The cluster analysis for this initial data can be in the form of centroid based clustering (i.e. k-means clustering) or even density-based clustering. An exemplary refinement is to analyze the data for long-scale periodic structure (such as weekly or monthly anomalies) including, but not limited to, techniques such as those described in the article *Detection and Characterization of Anomalies in Multivariate Time Series*, Cheng H., Tan, P.-N., Potter, C., and Klooster, S. A., Proceedings of the 2009 SIAM International Conference on Data Mining, 2009, incorporated herein by reference.

Exemplary systems incorporating aspects of embodiments of the invention can also contain an evaluation mode for quality control where the statistical data is compared to known a priori information. This is an external evaluation process that checks the results produced by such systems, enabling them to refine the event detection process and accuracy. The external evaluation need not, however, be performed continuously during ordinary operation of such systems. An exemplary evaluation process may compare the clusters produced by the statistical algorithms of the ordinary operation of a system to a benchmark metric using one, or more, statistical methods e.g. computing the Fowlkes-Mallows index, Rand measure etc. The a priori information used in these evaluations may be included in the calculation of the cluster centroids to produce a more precise personal behavior profile, but the a priori information is not required for proper operation during the ordinary operation of the system. In an exemplary implementation this evaluation is part of a quality control and software development process to assure that the algorithms are sufficiently robust and that no errors, either intentional or unintentional, have migrated into the software. Unlike conventional systems, the a priori knowledge required to conduct this evaluation is not a requirement for implementation.

What is claimed is:

1. A computer-implemented process for detecting and predicting events occurring to a person, comprising the steps of:
   receiving a first plurality of readings for location, orientation, velocity, and time of observation of a body part;
   applying a first statistical test to earliest readings in the first plurality of readings;
   applying the first statistical test to all later readings in the first plurality of readings;
   identifying at least one first cluster of n-dimensional behavior vectors as normal behavior from the earliest readings in the first plurality of readings, or in the earliest and in later readings in the first plurality of readings, or all of the first plurality of readings;
   collecting a second plurality of readings for location, orientation, velocity, and time of observation of the body part;
   constructing at least one second cluster of n-dimensional behavior vectors by applying the at least one first statistical test to the second plurality of readings;
   applying a second statistical test to determine if a deviation exists between the first plurality of readings and the second plurality of readings;
   determining whether an abnormal behavior exists with respect to at least one of the at least two parameters from the at least one first cluster of n-dimensional behavior vectors and the at least one second cluster of n-dimensional behavior vectors; and
   adding at least one reading making up the at least one second cluster of n-dimensional behavior vectors in chronological order to the latest reading making up the at least one first cluster of n-dimensional behavior vectors to thereby form the at least one first cluster of n-dimensional behavior vectors identified as normal behavior prior to collecting a new second plurality of readings.

2. The computer-implemented process of claim 1, wherein the step of determining further comprises identifying a future abnormal behavior likely to occur.

3. The computer-implemented process of claim 1, wherein the step of observing further comprises:
   sensing the parameter with respect to the person's head.

4. The computer-implemented process of claim 1, wherein the step of observing further comprises:
   sensing the parameter with respect to the person's torso.

5. The computer-implemented process of claim 1, wherein the step of observing further comprises:
   sensing the parameter with respect to one of the person's limbs.

6. The computer-implemented process of claim 1, wherein the step of observing further comprises:
   sensing the parameter with respect to a combination of two or more of the person's head, the person's torso, and one of the person's limbs, wherein the combination is less than needed to define the person's posture.

7. The computer-implemented process of claim 1, wherein the step of determining further comprises:
   identifying the combination of one or more readings corresponding to the abnormal behavior when at least one other body part is obscured from the sensor.

8. The computer-implemented process of claim 3, wherein the step of determining further comprises:
   identifying the combination of one or more readings corresponding to the abnormal behavior when at least one other body part is obscured from the sensor.

9. The computer-implemented process of claim 4, wherein the step of determining further comprises:
   identifying the combination of one or more readings corresponding to the abnormal behavior when at least one other body part is obscured from the sensor.

10. The computer-implemented process of claim 5, wherein the step of determining further comprises:
    identifying the combination of one or more readings corresponding to the abnormal behavior when at least one other body part is obscured from the sensor.

11. The computer-implemented process of claim 6, wherein the step of determining further comprises:
    identifying the combination of one or more readings corresponding to the abnormal behavior when at least one other body part is obscured from the sensor.

12. The computer-implemented process of claim 1, further comprising: computing velocity from a sequence of the readings.

13. The computer-implemented process of claim 1, further comprising: identifying a combination of readings corresponding to a normal event.

14. The computer-implemented process of claim 13, wherein the step of identifying a pattern for normal behavior further comprises: identifying a combination of readings representing an activity of daily living.

15. The computer-implemented process of claim 13, further comprising:
    learning to differentiate between the normal event and the abnormal behavior by applying a statistical test to the sequence of readings.

16. The computer-implemented process of claim 15, wherein the statistical test is correlation.

17. The computer-implemented process of claim 1, wherein the step of observing further comprises:
    sensing an output of a wearable sensor.

18. The computer-implemented process of claim 1, wherein the step of observing further comprises:
    sensing an output of one of: a visual camera and an infrared camera.

19. The computer-implemented process of claim 1, wherein the step of observing further comprises:
  sensing an output of a radio-wave measuring device.

20. The computer-implemented process of claim 1, wherein the step of observing further comprises: sensing an output of a light-wave measuring device.

21. The computer-implemented process of claim 1, further comprising: computing horizontal location from a sequence of the readings.

22. The computer-implemented process of claim 1, further comprising: computing vertical height from a sequence of the readings.

23. The computer-implemented process of claim 1, further comprising: computing orientation from a sequence of the readings.

24. The computer-implemented process of claim 2, wherein the step of determining further comprises:
  identifying the combination of one or more readings corresponding to the abnormal behavior when at least one other body part is obscured from the sensor.

* * * * *